United States Patent [19]

Joh

[11] Patent Number: 4,581,029
[45] Date of Patent: Apr. 8, 1986

[54] BLOOD PUMP
[75] Inventor: Yasushi Joh, Yokohama, Japan
[73] Assignee: Nippon Zeon Co., Ltd., Tokyo, Japan
[21] Appl. No.: 655,666
[22] Filed: Sep. 28, 1984
[30] Foreign Application Priority Data Sep. 28, 1983 [JP] Japan .................................. 58-178177

[51] Int. Cl.$^4$ .............................................. A61F 2/22
[52] U.S. Cl. ........................................ 623/3; 128/1 D
[58] Field of Search ............. 3/1.7; 128/1 D, DIG. 3, 128/64

[56] References Cited

U.S. PATENT DOCUMENTS 3,208,448 9/1965 Woodward .......................... 3/1.7 X
3,827,426 8/1974 Page et al. ........................... 3/1.7 X Primary Examiner—Richard J. Apley
Assistant Examiner—Alan W. Cannon
Attorney, Agent, or Firm—Armstrong, Nikaido, Marmelstein & Kubovcik

[57] ABSTRACT

The present invention relates to an artificial heart which comprises a housing, a brim forming a cover of the said housing, a blood introduction pipe and a blood discharge pipe which are incorporated as one piece with the said brim, a blood introduction valve and a blood discharge valve, respectively fitted to the said blood introduction pipe and the said blood discharge pipe and a blood chamber connected to the said brim and communicated with the said blood introduction pipe and the said blood discharge pipe.

In the present invention, the said brim is designed to be elastically deformable in accordance with pulsation of the said blood chamber so as to lighten the burdens of the said blood introduction valve and the said blood discharge valve.

3 Claims, 3 Drawing Figures

BLOOD PUMP

BACKGROUND OF THE INVENTION

1. Field of the invention

The present invention relates to a blood pump.

2. Description of the Prior Art

Researches on artificial hearts have been made worldwide. The artificial hearts subject to these researches are classified largely into two: one is a complete artificial heart which perfectly replaces the heart of a patient and the other is a supplementary artificial heart or blood pump which is used temporarily to assist the heart and to sustain the life of a patient, and which is removed, after restoring the function of his heart. Typically, they are used for ventricular assist. (Hereinafter, these two types of artificial hearts are generally called "artificial heart".) The researches on the artificial hearts have been actively underway in terms of function and safety. In particular, the antithrombosis materials are one of the essential factors in development of the artificial hearts. It is not going too far to say that development of the artificial hearts has been dependent upon development of antithrombosis materials. In addition to antithrombosis property, the mechanical properties of the materials are very important. Another important factor is the durability of heart valves which play a key role in the artificial heart.

The artificial heart must be characterized by the same function as that of a natural heart. In other words, the artificial heart must be designed so as to discharge blood at a pulsation similar to that of a natural heart. Therefore, the artificial heart is equipped with ports incorporating a valve. The artificial heart consists of at least a capacity-variable blood chamber, a blood introduction port and a blood discharge port which are connected with the blood chamber. Each of the blood introduction port and the blood discharge port has a valve preventing a counter flow of blood. When the blood chamber expands, the blood introduction valve opens and the blood discharge valve closes. On the other hand, when the blood chamber contracts, the blood introduction valve closes and the blood discharge valve opens so as to discharge blood through the blood discharge valve.

According to the differences in shape of a blood chamber and in contraction and expansion process, the artificial hearts can be classified into sack type, tube type, diaphragm type, pusher plate type, etc. The mechanism to introduce and discharge blood is as mentioned above and there remains no particular difference among the types.

So far there have been a variety of studies to determined what power is applied to the valves. As for a valve, for example, a disk-type Björk-Shiley valve, a blood chamber sufficiently filled with blood contracts instantaneously by an external pressure (normally 100 to 300 mm Hg), thereby pushing the discharge valve open so as to discharge instantaneously blood against aorta pressure. Then the stent (a valve support rod) crashes into the valve disk. When the blood chamber expands after discharging blood, the pressure in the blood chamber becomes negative and a pressure of 100 to 300 mm Hg then formed on the artery side is applied smashingly to the valve in the adverse direction. This forms a blood hammer, which strikes the valve. (In general, such an impact liquid force is called "water hammer".) The severe shock like this is repeated as much as the pulsation of a heart, that is, approx. 100,000 beats daily, approx. 3 million beats monthly or approx. 40 million beats yearly. This phenomenon can be seen also in the blood introduction valve. When the blood chamber of an artificial heart expands, this valve opens with a pressure of approx. 50 mm Hg at the left atrium. Nevertheless, when the blood chamber contracts, a pressure of 100 to 300 mm Hg is applied smashingly in the adverse direction. This shock to the valve is applied to the valve disk and also to the valve-supporting stent. The frequency of shock amounts to 100,000 or more, hence making it difficult to take adequate safety measures against breakage of valves due to shock. Artificial heart valves now commercialized for replacement of natural ones can work as long as about 5 years, or can open and close at least 200 million times. Most of the artificial hearts so far developed around the world employ such commercialized artificial heart valves for the purpose of replacing natural ones from a safety viewpoint.

Very interesting and very important is it in that an artificial heart valve which has been quite safe in replacement of a natural one, may cause many unexpected troubles, for example, removal of a valve disk, damage of a disk and stent, when it is incorporated in an artificial heart.

BRIEF SUMMARY OF THE INVENTION

Accordingly, an object of the present invention is to provide an artifical heart or blood pump designed to permit reduction of shocks onto the artificial heart valves.

The above-mentioned objects can be attained as follows. In the present invention, the artificial heart comprises a housing, a brim forming a cover of the said housing, a blood introduction pipe and a blood discharge pipe which are incorporated as one piece with the said brim, a blood introduction valve and a blood discharge valve which are respectively mounted at the said blood introduction pipe and the said blood discharge pipe, and a blood chamber which is connected to the said brim and communicated with the said blood introduction pipe and the said blood discharge pipe. In this artificial heart, the said brim is designed so as to be subject to elastic deformation.

Other and further objects of this invention will become obvious upon an understanding of the illustrative embodiment about to be described or will be indicated in the appended claims, and various advantages not referred to herein will occur to one skilled in the art upon employment of the invention in practice.

DESCRIPTION OF THE PREFERRED EMBODIMENT

The inventor of the present invention has investigated reasons why the artificial heart valves are susceptible to troubles, if they are set to an artificial heart, while they show good results when they replace natural heart valves. As a result, the inventor has provided the artificial hearts with a dynamic behavior similar to that of the natural hearts, thereby succeeding in materialization of the present invention. The natural heart is totally composed of a soft muscular tissue and move flexibly. In accordance with pulsation, the heart moves softly in the thorax in which the heart is situated. Therefore, when a cardiac muscle contracts or expands, namely a valve opens or closes, the cardiac muscle works to absorb a great shock by its flexible movement. In other words, the heart which can be considered as an shock absorber, absorbing the shock produced to the heart by a total movement of the heart. In the artificial heart, on the other hand, the blood chamber is made of a flexible tissue changeable in capacity. But the valve fixed portion thereof is solid and has no function to absorb the shock and no conception to realize it.

Taking these points into consideration, the inventor of the present invention has succeeded in clearing the troubles proper to the valves and in completing the present invention, by making the pipes fixing the valves movable in a shock-absorbing direction.

An embodiment in which the present invention is applied to a sack-type artificial heart will be described below with reference to the drawings. Sack-type artificial hearts or blood pumps are described in applicant's co-pending application Ser. No. 319,718, which is incorporated by reference.

Figure 1:
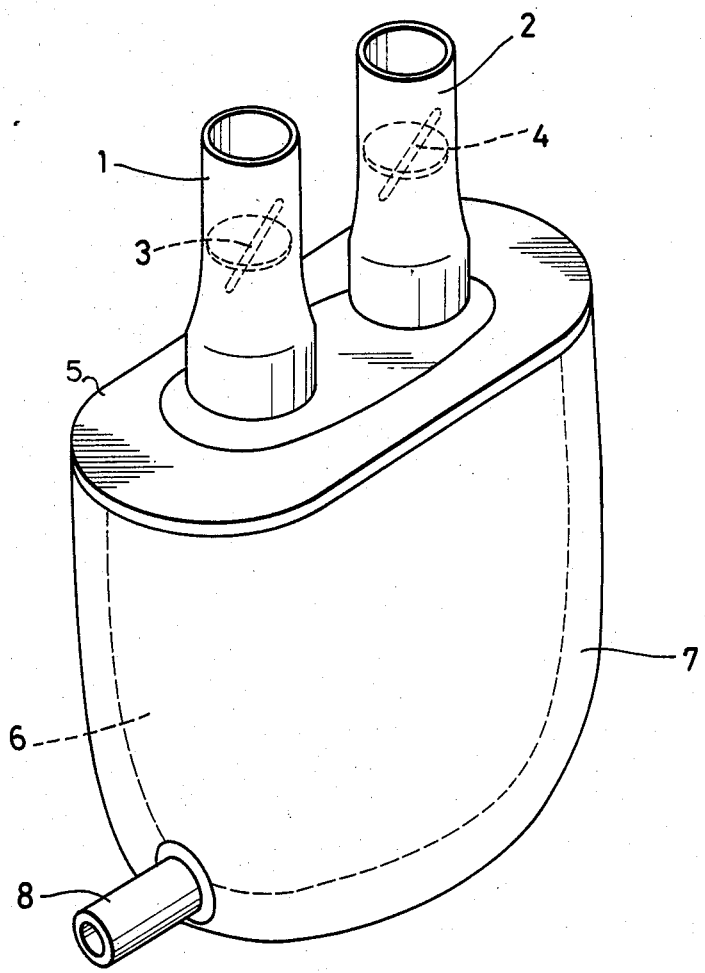
FIG. 1 is a perspective view of an artificial heart according to an embodiment of the present invention.

FIG. 1 is a perspective view of the sack-type artificial heart. Pipes 1 and 2 which fix a blood introduction valve 3 and a blood discharge valve 4 therein are fitted to the elastic and flexible brim 5, which functions as a cover of an outer case 7 and is formed integrally with a blood chamber 6 and the blood introduction and discharge pipes 1 and 2. The blood introduction pipe is attached by a cannulae to the appropriate atrium and the discharge pipe 2, by cannula, to the pulmonary artery or aorta.

The operation of the artificial heart is made by change of air pressure: the air into or from an air introduction and discharge port 8 of the outer case 7 causes pressurization and decompression repeatedly, thereby contracting or expanding the blood chamber 6 so as to discharge blood.

Figure 3:
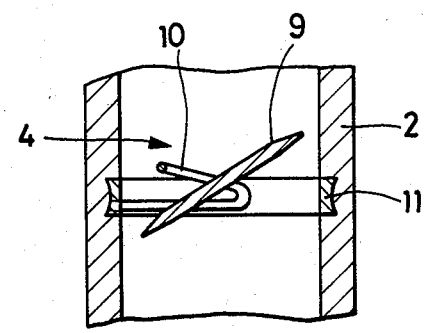
FIG. 3 is an enlarged partial cross section of a blood discharge pipe.

Referring now to blood discharge operation, on a phase of diastole of the blood chamber 6, namely when discharging blood instantaneously just at the changing point from decompression to pressurization, both blood discharge valve 4 and blood introduction valve 3 receive an outward, namely upward impact pressure. The blood discharge valve 4 then opens. The disk 9 of the opened valve collides heavily with the stent 10 (valve support rod) which supports the disk and controls the opening of the disk, as shown in FIG. 3. The blood introduction valve 3 is then closed and the disk thereof collides heavily with the valve ring support 11.

Figure 2:
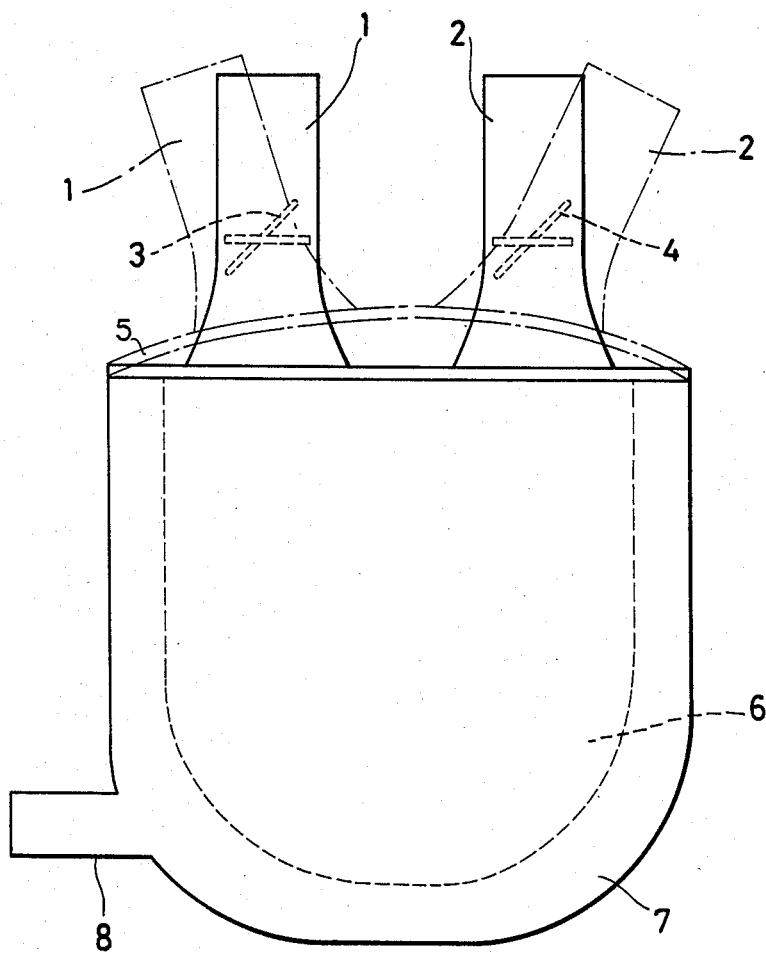
FIG. 2 is a front view of the same.

In this embodiment, the blood introduction pipe 1, the blood discharge pipe 2 and the brim 5 are formed into one piece. Therefore, when blood is discharged, the same positive pressure is also applied to the brim 5 which forms a cover of the pump. In this case, the brim 5, the blood introduction pipe 1 and the blood discharge pipe 2 are made of elastic material. Therefore, the brim 5 is bent upward, as shown in an imaginary line of FIG. 2, because of the above-mentioned positive pressure, while the pipes 1 and 2 are inclined upward on end, as shown in a imaginary line of the same drawing. The elastic behavior corresponding to pressure permits to prevent a direct shock to the valves, hence clearing successfully the said troubles proper to the valves.

The artificial heart of this embodiment is made of plasticized polyvinyl chloride, namely polyvinyl chloride containing a plasticizer. That is, the brim 5, the blood introduction pipe 1 and the blood discharge pipe 2 contain, as plasticizer, dioctyl phthalate of 70 parts by weight to 100 parts by weight of polyvinylc chloride. Besides, to gain more flexibility, the blood chamber 6 contains 85 parts by weight of plasticizer to 100 parts by weight of polyvinyl chloride. Because of this construction, as already mentioned above, as the pump pulsates, the pump brim 5 moves due to its flexibility and this flexible movement can absorb a shock exerted on the valves 3 and 4. In this case, it has been found to be essential to design a shift of the valve position of at least 0.2 mm, preferably within a range of 0.2 mm and 8 mm. If this shift is less than 0.2 mm, little shock-absorbing effect can be expected, while a too much shift exceeding 8 mm will result in an undesirable mechanical destruction of materials.

If the brim is made of polyvinyl chloride containing plasticizer, to allow the said shift of the valve, it is necessary to contain 40 to 120 (preferably 50 to 90) parts by weight of plasticizer to 100 parts by weight of polyvinyl chloride. As the plasticizer, the known plasticizers of polyvinyl chloride may be used. From the viewpoint of nontoxity, dioctyl phthalate, dioctyl adipate, etc. are preferred. The brim of the present invention can be made also of polyurethane. In this case, the type of polyurethane is not limitative, and thereof either polyester polyurethane or polyether polyurethane can be applied.

Polyester polyurethane may be prepared by chain extension, with a known chain extending agent, of prepolymers of which both ends are isocyanate groups. The prepolymers can be obtained by reacting a polyester having a hydroxy group at its end, which is made by synthesizing glycol such as ethylene glycol and diethylene glycol or polyvalent alcohol such as trimethylolpropane and glycerin and polyvalent carboxylic acid such as adipic acid and succinic acid, with a compound containing an isocyanate which has been so far used for preparation of polyurethane such as ethylene diisocyanate, 2,4-trilene diisocyanate, 4,4'-diphenylmethane diisocyanage, etc.

Polyether polyurethane may be prepared by molecular chain extension, with a known chain extending agent, of prepolymers of end isocyanate which is made through reaction of the afore-mentioned isocyanate with the polyol which is obtained by reacting polyethylene glycol, polypropylene glycol or copolymers thereof, or tetramethylene glycol, polytetramethylene glycol or alkylene oxide, with a polyvalent alochol such as propylene glycol, 1,2,6-hexane triol, etc.

In preparation of polyurethane used for the present invention, it is possible to produce polyurethane urea by using, as a chain extending agent, diamine including ethylene diamine, diethylene diamine and hexamethylene diamine. It is also a matter of course that the known diol such as ethylene glycol and butanediol can be used as chain extending agents.

The thickness of the brim may be used from 1 mm to 10 mm, preferably 3 mm to 8 mm. If the said thickness is less than this range, the strength of the brim will be reduced, while the brim becomes less movable if the said thickness surpasses this range, which will make it difficult to attain the objects of the present invention.

In the present invention, where the fixed part of the valves is designed to move according to the pulsation of the blood pump to absorb shock, as already described above, there has been no damage to the valves, which is proved in the examples mentioned hereafter. Based on the above-mentioned facts, it can be considred that the present invention has a deep significance in terms of safety, when putting the artificial harts into practical use.

EXAMPELS 1 TO 8

An experiment was carried out with goats on the artificial heart shown in FIG. 1, where the blood introduction pipe 1 and blood discharge pipe 2 are connected with the blood chamber 6 through the movable brim 5 made of polyvinyl chloride containing different ratios of plasticizers, with the use of a pump which incorporates, as one piece, the said blood introduction pipe and blood discharge pipe into the brim 5. The result of this experiment is summerized in Table 1.

In this case, the blood chamber (sack part) is made of polyvinyl chloride containing 80 parts by weight of dioctyl adipate (DOP) and the pulsation was 100 beats per minute. The valve used was a Björk-Shiley valve.

TABLE 1

| Example | Composition of Brim (DOP Content per 100 parts by weight of PVC) | Thickness of Brim (mm) | Test Period (month) | Condition of Valve |
|---|---|---|---|---|
| 1 | DOP 80 | 5 | 3 | Normal |
| 2 | DOP 70 | 5 | 3 | Normal |
| 3 | DOP 90 | 5 | 3 | Normal |
| 4 | DOP 80 | 8 | 8 | Normal |
| 5 | DOP 90 | 8 | 2 | Normal |
| 6 | DOP 80 | 7 | 8 | Normal |
| 7 | DOP 70 | 7 | 2 | Normal |
| 8 | DOP 40 | 2 | 2 | Normal |

EXAMPLE 9

A sack-type artificial heart was prepared with the brim 5 made of polyether polyurethane (Estene 5714 made by GOODRICH Co.) into 5 mm-thickness. A mock test was made on this artificial heart at a temperature of 37° C., at a pulsation of 100 beats per minute, by using an aqueous solution containing 10% glycerin in place of blood. The series of 6-month long tests showed no sign of valve damage.

As known from Examples 1 to 9, with the brim of a certain quality and thickness pulsation due to expansion and contraction of the pump is absorbed by flexure of the brim. Furthermore, the shift of the valve position was stable in every example within a range from 0.5 mm to 4 mm, showing no abnormality on the valves.

COMPARATIVE EXAMPLE

In the sack-type artificial heart used in Example 1, two versions were prepared: the brims of these versions contained 15 and 30 parts by weight of DOP, respectively (to 100 parts by weight of PVC) and were 15 mm thick and the other conditions were same to those of Example 1. Three samples for each example were subject to one-month long mock test at a pulsation of 100 beats per minute. Damaged valves were confirmed in three samples of the example containing DOP of 15 parts by weight and in two samples of the example containing DOP of 30 parts by weight.

What is claimed is:
1. A blood pump comprising:
 (a) a rigid housing;
 (b) a brim portion attached to said housing;
 (c) a blood chamber in the form of a flexible sac integrally joined to said brim and projecting into said housing;
 (d) a blood introduction pipe integrally formed with said brim and projecting outside said rigid housing;
 (e) a disk-type introduction valve situated within said blood introduction pipe;
 (f) a blood discharge pipe integrally formed with said brim and projecting outside of said rigid housing; and
 (g) a disk-type discharge valve situated within said blood discharge pipe
wherein said brim is formed from an elastically deformable, non-thrombogenic material having a thickness between about 1 and about 10 mm and allowing a movement of said introduction and discharge valves of between 0.2 and 8.0 mm during the systolic and diastolic phases of pumping.

2. A blood pump according to claim 1, in which the brim is formed from polyvinyl chloride and 40–120 parts of a plastisizer per 100 parts by weight of polyvinyl chloride.

3. An artificial heart according to claim 1, in which the brim is made of polyurethane.

* * * * *